United States Patent [19]

Boulogne et al.

[11] 4,126,675

[45] Nov. 21, 1978

[54] NAIL POLISHES

[75] Inventors: Jean Boulogne, L'Hay les Roses; Christos Papantoniou, Epinay sur Seine, both of France

[73] Assignee: L'Oreal, Paris, France

[21] Appl. No.: 795,372

[22] Filed: May 9, 1977

[30] Foreign Application Priority Data

May 13, 1976 [FR] France .................................. 76 14430

[51] Int. Cl.² .......................... A61K 7/04; C08L 33/10
[52] U.S. Cl. ....................................... 424/61; 526/330
[58] Field of Search .......................... 424/61; 526/330

[56] References Cited

U.S. PATENT DOCUMENTS

| 3,478,756 | 11/1969 | Sautter et al. | 424/61 |
| 3,630,984 | 12/1971 | Sheetz | 526/330 |
| 3,749,769 | 7/1973 | Sugiyama et al. | 424/61 |
| 3,849,547 | 11/1974 | Kalopissis | 424/61 |
| 3,860,552 | 1/1975 | Montillier | 526/330 |

FOREIGN PATENT DOCUMENTS 516,788 1/1940 United Kingdom ...................... 424/61

*Primary Examiner*—Donald B. Moyer
*Attorney, Agent, or Firm*—Stevens, Davis, Miller & Mosher

[57] ABSTRACT

New nail polish compositions including a resin, a plasticizer, a solvent system, a filming agent, and optionally colorants, wherein the resin is a copolymer of methyl methacrylate and hexyl methacrylate.

15 Claims, No Drawings

NAIL POLISHES

The present invention relates to new nail polishes, which polishes exhibit good adhesion, long life and excellent brilliance.

It has already been proposed to use as nail polishes certain copolymers, particularly of butyl polymethacrylate or a copolymer of methyl methacrylate/butyl methacrylate with the goal of improving the appearance of the nails and likewise their adherence.

Additionally, it has equally been proposed to use acrylate/methacrylate copolymers especially copolymers of butyl acrylate/2-hydroxy ethyl methacrylate with the object of replacing the conventional synthetic resins used as nail polishes, and in particular the aryl sulfonamide formaldehyde resins such as, for example, the resins sold under the commercial names "Santolite MHP" or "Santolite MS 80".

Although these copolymers were able to achieve a polish of better quality than those previously obtained, it has turned out to be quite difficult to obtain simultaneously good adhesion and excellent brilliance.

After significant research we have come to state that these two properties of much importance for nail polishes may be obtained when one uses as the resin therein a copolymer of methyl methacrylate and hexyl methacrylate.

By the use of this type of copolymer it also is noted that it is possible to use a very much reduced quantity of film producing agents and even in certain cases totally to suppress them without so much as ascertaining an appreciable diminution of the properties of the polish.

The conventional film producing agents used in nail polishes are nitrocellulose, and most particularly the nitrocelluloses designated under the abbreviations "RS" or "SS".

The ability to employ reduced quantities of nitrocellulose and in certain cases to avoid its use provides a number of advantages because those products are dangerous to handle and stock.

The fact that according to the invention the copolymers of methyl methacrylate and hexyl methacrylate serve to replace resins of the aryl sulfonamide formaldehyde type also presents an advantage which is not negligible because such resins sometimes exhibit a certain aggressiveness and allergic phenomena due to the liberation of formol.

The present invention has for its named objective as a new industrial product a nail polish characterized by the fact that it comprises as its resin a copolymer of methyl methacrylate and hexyl methacrylate.

The copolymers employed preferably comprise from 10 to 95% by weight methyl methacrylate and from 5 to 90% by weight hexyl methacrylate.

According to a particular method of realization, the copolymers comprised from 20 to 90% by weight methyl methacrylate and from 10 to 80% by weight hexyl methacrylate.

According to another form of realization, the copolymers of methyl methacrylate and hexyl methacrylate may be reticulated with the aid of a reticulating agent present in a proportion of 0.01 to 1% by weight of the amount of monomers present. As such reticulating agents there may be used, for example, the group consisting of: dimethacrylate of ethylene glycol and diacrylate of ethylene glycol.

The copolymers of methyl methacrylate and hexyl methacrylate, reticulated or not, have a molecular weight of between 5,000 and 150,000, and preferably between 8,000 and 60,000.

The nail polishes according to the present invention preferably comprise:

i. 6 to 35% by weight of a copolymer of methyl methacrylate and hexyl methacrylate;
ii. at least from 5 to 8% by weight of a plasticizer;
iii. at least from 0 to 12% by weight of a film producing agent;

the remainder consists essentially of the solvent system, which comprises the usual solvents and/or conventional diluents for this type of composition.

When the polish contains nitrocellulose it is generally present in a quantity comprising between 6 and 12% by weight and in that case the polish contains a proportion of copolymer comprising between 6 and 12% by weight.

When the polish does not contain nitrocellulose, in that case the proportion of copolymer is greatly elevated and generally comprises between 20 and 35% by weight.

The nitrocelluloses used are as indicated above preferably the nitrocelluloses of the type "RS" or "SS", and in particular nitrocellulose type RS ¼ seconds, nitrocellulose type RS ½ seconds, and nitrocellulose RS type ¾ seconds.

"RS" type nitrocelluloses contain about 11.2 to 12.8% nitrogen and are soluble in esters such as ethyl acetate and its homologues, ketones, and ethers of glycol. "SS" type nitrocelluloses contain about 10.7 to 11.2% nitrogen and are soluble in mixtures of alcohol and toluene.

The "RS" type nitrocelluloses are preferable for use in the present invention.

As plasticizing agents one preferably uses tricresyl phosphate, benzyl benzoate, tributyl phosphate, butyl acetyl ricinoleate, glyceryl acetyl ricinoleate, dibutyl phthalate, dibutyl glycolate, dioctyl phthalate, butyl stearate, tributoxy ethyl phosphate, triphenyl phosphate, triethyl citrate, tributyl citrate, tributyl acetyl citrate, 2-hexyl triethyl acetyl citrate, dibutyl tartarate, dimethoxy ethyl phthalate, di-isobutyl phthalate, diamyl phthalate, camphor and various mixtures thereof.

Among the solvents useable in the compositions of the polishes, a few in particular are cited: acetone, ethyl acetate, butyl acetate, methyl glycol acetate, methyl ethyl ketone, methylisobutylketone, methyl acetate, or mixtures of such solvents.

As diluents one preferably uses toluene or xylene in a proportion generally comprising between 10 and 30% by weight of the total polish.

When the polishes contain a certain quantity of nitrocellulose one also introduces to the solvent system a coupler or co-solvent in a proportion of 1 to 15%, and a few among such couplers or co-solvents are: ethanol, n-butanol, n-propanol, isopropanol, and mixtures thereof.

In the polishes according to the invention the solvent system comprises 60 to 80% by weight of the polish.

If one wishes to obtain colored polishes, it is possible to introduce into the base polish coloring agents such as those currently employed in these types of compositions.

Among these agents a few in particular are cited: the D and C Red Nos. 10, 11, 12 and 13; the D and C Red No. 7, the D and C Red Nos. 5 and 6; the D and C Red No. 34; lakes such as the lake D and C Yellow No. 5 and the lake D and C Red No. 2. In addition to these organic coloring agents, it is also possible to use inorganic substances such as titanium dioxide, bismuth oxychloride, brown iron oxide, red iron oxides, and in the same way guanine.

According to one variation it is also possible to introduce as coloring agents colored polymers such as those described in U.S. Pat. No. 3,849,547.

The coloring agents are generally present in the polish composition in a proportion comprising between 0.05% and 6% and preferably between 1 and 3% by weight of the total polish.

In accordance with the objective of avoiding sedimentation of the coloring agents it is possible to add to the polishes clays of the montmorillonite type such as "Bentone 27" (benzyl-dodecyl-dimethyl-ammonium-montmorillonite) or "Bentone 38" (dimethyl-dioctadecyl-ammonium-montmorillonite) in the presence of a swelling agent such as orthophosphoric acid.

Although the methyl methacrylate/hexyl methacrylate copolymers themselves have been known, we give as illustrations of the aforementioned invention certain examples of the preparation of these copolymers and diverse examples of nail polishes made using these copolymers.

EXAMPLE I

Preparation of a 30%/70% methyl methacrylate/-hexyl methacrylate copolymer:

Into a one liter flask provided with a mechanical agitator, a thermometer and an inflow of nitrogen, one introduces 30g. of methyl methacrylate, 70g of hexyl methacrylate and 2g of benzoyl peroxide in solution with 100 g of ethyl acetate. The reaction mixture is heated under agitation with reflux for 24 hours.

After cooling the solution is slowly poured into 3 liters of methanol and then filtered. The polymer is dried at 50° C. under reduced pressures.

One obtains 75g of pure polymer.

Yield: 75%

$\overline{M}n$ = 38,000 (by osmometry in solution with toluene).

Example II

Preparation of a 20%/80% methyl methacrylate/-hexyl methacrylate copolymer:

This copolymer is prepared according to the same procedure as described in Example I above, except with 20g of methyl methacrylate and 80g of hexyl methacrylate.

Yield: 70%

$\overline{M}n$ = 39,000 (by osmometry in solution with toluene).

Example III

Preparation of a 90%/10% methyl methacrylate/-hexyl methacrylate copolymer:

This copolymer is prepared according to the same procedure as described in Example I above, except with 10g of hexyl methacrylate and 90g of methyl methacrylate.

Yield: 60%

$\overline{M}n$ = 45,000 (by osmometry in toluene).

EXAMPLES OF NAIL POLISHES

EXAMPLE A

One prepares a colorless nail polish according to the invention by mixing the following ingredients:

| | |
|---|---|
| Nitrocellulose RS ¼ seconds | 16g. |
| Copolymer prepared according to Example I | 6g. |
| Ethyl alcohol | 4g. |
| Butyl alcohol | 4g. |
| Camphor | 2g. |
| Butyl phthalate | 4g. |
| Toluene | 20g. |
| Ethyl acetate | 10g. |
| Butyl acetate | 34g. |
| | 100g. |

This base polish applied on the nails exhibits very good adhesion and excellent enduring brilliance

EXAMPLE B

One prepares a colored nail polish according to the invention by mixing the following ingredients:

| | |
|---|---|
| The colorless polish described in Example A | 96.88g. |
| Bentone 27 (benzyl-dodecyl-dimethylammonium-montmorillonite) | 1g |
| Phosphoric acid | 0.02g. |
| Titanium oxide | 1g. |
| D and C Red No. 7 | 0.4g. |
| D and C Red No. 11 | 0.2g. |
| D and C Red No. 5 | 0.3g. |
| Red iron oxide | 0.2g. |
| | 100g. |

This colored nail polish applied on the nails exhibits excellent brilliance and very good adhesion.

EXAMPLE C

One prepares a colorless nail polish according to the invention by mixing the following ingredients:

| | |
|---|---|
| Nitrocellulose RS ¼ seconds | 12g. |
| Copolymer prepared according to Example II | 10g. |
| Ethyl alcohol | 3g. |
| Butyl alcohol | 3g. |
| Camphor | 2g. |
| Butyl phthalate | 3g. |
| Triethyl acetylcitrate | 2g. |
| Toluene | 15g. |
| Ethyl acetate | 15g. |
| Butyl acetate | 35g. |
| | 100g. |

EXAMPLE D

One prepares a pearly nail polish according to the invention by mixing the following ingredients:

| | |
|---|---|
| The colorless polish obtained according to Example C | 97.35g. |
| Bentone 38 (dimethyl-dioctadecyl-ammonium-montmorillonite) | 1.5g. |
| Phosphoric acid | 0.02g. |
| Guanine | 1g. |
| D and C Red No. 7 | 0.05g. |
| Lake D and C Yellow No. 5 | 0.05g. |
| D and C Red No. 11 | 0.03g. |
| | 100g. |

EXAMPLE E

One prepares a colorless nail polish according to the invention by mixing the following ingredients:

| | |
|---|---|
| Copolymer prepared according to Example I | 25g. |
| Toluene | 20g. |
| Ethyl acetate | 20g. |
| Butyl acetate | 35g. |
| | 100g. |

EXAMPLE F

One prepares a colored nail polish according to the invention by mixing the following ingredients:

| | |
|---|---|
| Colorless polish according to Example E | 96.69g |
| Bentone 27 | 1.2g. |
| Phosphoric acid | 0.01g. |
| Titanium oxide | 0.8g. |
| D and C Red No. 7 | 0.5g. |
| D and C Red No. 11 | 0.4g. |
| Brown iron oxide | 0.4g. |
| | 100g. |

EXAMPLE G

One prepares a colorless nail polish according to the invention by mixing the following ingredients:

| | |
|---|---|
| Copolymer prepared according to Example II | 30g. |
| Toluene | 10g. |
| Ethyl acetate | 15g. |
| Methylethylketone | 10g. |
| Butyl acetate | 30g. |
| Methylglycol acetate | 5g. |
| | 100g. |

EXAMPLE H

One prepares a pearly nail polish according to the invention by mixing the following ingredients:

| | |
|---|---|
| Colorless polish obtained according to Example G | 97.6g. |
| Bentone 38 | 1g. |
| Bismuth oxychloride | 0.8g. |
| D and C Red No. 7 | 0.3g. |
| D and C Red No.6 | 0.2g. |
| Lake D and C Yellow No. 5 | 0.1g. |
| | 200g. |

This colored polish applied on the nails exhibits good brilliance and long life.

EXAMPLE X

One prepares a colorless nail polish according to the invention by mixing the following ingredients:

| | |
|---|---|
| Copolymer prepared according to Example III | 25g. |
| Toluene | 31g. |
| Butyl actate | 14g. |
| Ethyl acetate | 25g. |
| Glycreryl acetyl ricinoleate | 5g. |
| | 100g. |

EXAMPLE J

One prepares a colored nail polish according to the invention by mixing the following ingredients:

| | |
|---|---|
| Colorless polish obtained according to Example X | 96.78g. |
| Bentone 27 | 1g. |
| Phosphoric acid | 0.02g. |
| Titanium oxide | 0.9g. |
| D and C Red No. 7 | 0.4g. |
| D and C Red No. 11 | 0.3g. |
| Lake D and C Yellow No.5 | 0.6g. |
| | 100g. |

This colored polish applied on the nails exhibits good adhesion and good brilliance.

EXAMPLE K

One prepares a colorless nail polish according to the invention by mixing the following ingredients:

| | |
|---|---|
| Copolymer prepared according to Example III | 25g. |
| Butyl acetate | 15g. |
| Ethyl acetate | 30g. |
| Toluene | 5g. |
| Methylethylketone | 20g. |
| Dimethoxy ethyl phthalate | 5g. |
| | 100g. |

EXAMPLE L

One prepares a pearly nail polish according to the invention by mixing the following ingredients:

| | |
|---|---|
| Colorless polish obtained according to Example K | 97.3g. |
| Bentone 38 | 1g. |
| Bismuth oxychloride | 0.5g. |
| D and C Red No. 7 | 0.3g. |
| D and C Red No. 11 | 0.4g. |
| Lake of D and C Yellow No. 5 | 0.5g. |
| | 100g. |

What is claimed is:

1. A nail polish comprising a resin, a plasticizer, a solvent system and a filming agent, wherein the resin comprises a copolymer of 10 to 95% by weight methyl methacrylate and of 5 to 90% by weight hexyl methacrylate.

2. The polish of claim 1, wherein said copolymer comprises 20 to 90% by weight methyl methacrylate and 10 to 80% by weight hexyl methacrylate.

3. The polish of claim 1, wherein the copolymer is reticulated with a reticulating agent used in an amount between 0.01 and 1% by weight of the initial monomers.

4. The polish of claim 3, wherein the reticulating agent is selected from the group consisting of: ethylene glycol dimethacrylate and ethylene glycol diacrylate.

5. The polish of claim 1, wherein the solvent system comprises 60 to 80% by weight of the total polish.

6. The polish of claim 5, wherein the solvent system contains a coupler or co-solvent present in an amount betweem 1 and 15% by weight of the total polish.

7. The polish of claim 1, additionally comprising a coloring agent.

8. The polish of claim 7, wherein said coloring agent is organic.

9. The polish of claim 7, wherein said coloring agent is inorganic.

10. The polish of claim 8, wherein said coloring agent is a colored copolymer.

11. The polish of claim 7 wherein said coloring agent comprises between 0.05% and 6% by weight of the total polish.

12. The polish of claim 13, wherein said coloring agent comprises between 1 and 3% by weight of the total polish.

13. The polish of claim 1, comprising:
6 to 35% by weight of said copolymer;
at least 5 to 8% by weight of a plasticizer;
at least 0 to 12% by weight of a film forming agent;
the remainder consisting essentially of the solvent system.

14. The polish of claim 1, comprising:
6 to 12% by weight of said copolymer;
at least 5 to 8% by weight of a plasticizer;
at least 6 to 12% by weight of a film forming agent;
the remainder consisting essentially of the solvent system.

15. The polish of claim 1, comprising:
20 to 35% by weight of said copolymer;
at least 5 to 8% by weight of a plasticizer;
the remainder consisting essentially of the solvent system.

* * * * *